(12) United States Patent
Centanni (10) Patent No.: US 7,611,667 B2
(45) Date of Patent: Nov. 3, 2009

(54) APPARATUS FOR CONTROLLING THE CONCENTRATION OF A STERILANT CHEMICAL IN A FLUID

(75) Inventor: Michael A. Centanni, Parma, OH (US)

(73) Assignee: STERIS Corporation, Mentor, OH (US)

( * ) Notice: Subject to any disclaimer, the term of this patent is extended or adjusted under 35 U.S.C. 154(b) by 170 days.

(21) Appl. No.: 11/899,490

(22) Filed: Sep. 6, 2007

(65) Prior Publication Data

US 2008/0063574 A1 Mar. 13, 2008

Related U.S. Application Data

(62) Division of application No. 10/853,084, filed on May 25, 2004.

(51) Int. Cl.
| | |
|---|---|
| A61L 9/00 | (2006.01) |
| G05B 1/00 | (2006.01) |
| A61L 2/00 | (2006.01) |
| B09B 3/00 | (2006.01) |
| A62D 3/00 | (2007.01) |
| G01N 21/00 | (2006.01) |
| G01N 19/10 | (2006.01) |

(52) U.S. Cl. .............. 422/28; 422/33; 422/29; 422/34; 422/105; 422/119; 422/292; 422/295; 422/305; 588/299; 588/300; 588/900; 73/1.02; 73/23.2; 73/DIG. 2; 73/DIG. 4

(58) Field of Classification Search .......... 422/28, 422/33, 29, 34, 105, 119, 292, 295, 305; 588/299–300, 900; 73/1.02, 23.2, DIG. 2, 73/DIG. 4
See application file for complete search history.

(56) References Cited

U.S. PATENT DOCUMENTS

| | | | |
|---|---|---|---|
| 3,164,004 A | 1/1965 | King, Jr. ................. | 73/23 |
| 3,327,519 A | 6/1967 | Crawford ............... | 73/23 |
| 3,464,797 A | 9/1969 | Hagopain | |
| 3,636,444 A | 1/1972 | Strawn et al. ........... | 324/61 |
| 3,778,706 A | 12/1973 | Thompson .............. | 324/61 |
| 4,145,186 A | 3/1979 | Anderson ............... | 23/232 |
| 4,163,384 A | 8/1979 | Blakemore ............. | 73/29 |
| 4,219,776 A | 8/1980 | Arulanandan .......... | 324/323 |
| 4,236,893 A | 12/1980 | Rice ....................... | 23/230 B |
| 4,242,096 A | 12/1980 | Oliveira et al. ......... | 23/230 B |
| 4,314,821 A | 2/1982 | Rice ....................... | 23/230 B |
| 4,427,772 A | 1/1984 | Kodera et al. .......... | 435/27 |

(Continued)

OTHER PUBLICATIONS

U.S. Appl. No. 10/456,378, filed Jun. 6, 2003, Centanni, entitled: Method and Apparatus for Formulating and Controlling Chemical Concentrations in a Solution.

(Continued)

*Primary Examiner*—Jill Warden
*Assistant Examiner*—Monzer R Chorbaji
(74) *Attorney, Agent, or Firm*—Kusner & Jaffe; Michael A. Centanni (57) ABSTRACT

A sterilization system that includes a sensor for determining the concentration of a liquid sterilant in a sterilant fluid. The sterilant fluid is comprised of a blend of sterilant fluids from a plurality of sterilant supplies. The concentration of the liquid sterilant differs in each of the sterilant supplies. The sensor allows a controllable concentration of liquid sterilant to be supplied to a vaporizer.

11 Claims, 4 Drawing Sheets

U.S. PATENT DOCUMENTS

| | | | | |
|---|---|---|---|---|
| 4,525,265 | A | 6/1985 | Abe et al. | 204/403 |
| 4,674,879 | A | 6/1987 | Gregorig et al. | 356/301 |
| 4,788,466 | A | 11/1988 | Paul et al. | 310/316 |
| 4,843,867 | A | 7/1989 | Cummings | 73/23 |
| 4,849,178 | A | 7/1989 | Azuma | 422/69 |
| 4,857,152 | A | 8/1989 | Armstrong et al. | 204/1 T |
| 5,157,968 | A | 10/1992 | Zfira | 73/149 |
| 5,243,858 | A | 9/1993 | Erskine et al. | 73/204.26 |
| 5,339,675 | A | 8/1994 | DiLeo et al. | 73/24.04 |
| 5,364,510 | A | 11/1994 | Carpio | 204/153.1 |
| 5,439,569 | A | 8/1995 | Carpio | 204/153.1 |
| 5,459,568 | A | 10/1995 | Yano et al. | 356/336 |
| 5,470,754 | A | 11/1995 | Rounbehler et al. | 436/106 |
| 5,595,908 | A | 1/1997 | Fawcett et al. | 435/287.2 |
| 5,600,142 | A | 2/1997 | Van Den Berg et al. | 250/339.13 |
| 5,700,375 | A | 12/1997 | Hagen et al. | 210/651 |
| 5,756,631 | A | 5/1998 | Grate | 528/26 |
| 5,843,307 | A | 12/1998 | Faivre et al. | 210/192 |
| 5,847,276 | A | 12/1998 | Mimken et al. | 73/453 |
| 5,856,198 | A | 1/1999 | Joffe et al. | 436/100 |
| 5,866,798 | A | 2/1999 | Schönfeld et al. | 73/24.06 |
| 5,882,590 | A * | 3/1999 | Stewart et al. | 422/28 |
| 5,958,787 | A | 9/1999 | Schönfeld et al. | 436/116 |
| 6,156,267 | A | 12/2000 | Pai et al. | 422/3 |
| 6,171,867 | B1 * | 1/2001 | Feucht et al. | 436/124 |
| 6,196,052 | B1 | 3/2001 | May et al. | 73/24.06 |
| 6,369,387 | B1 | 4/2002 | Eckles | 250/343 |
| 6,410,332 | B1 | 6/2002 | Desrosiers et al. | 436/37 |
| 6,454,874 | B1 | 9/2002 | Jacobs et al. | 134/18 |
| 6,560,551 | B1 | 5/2003 | Severson et al. | 702/54 |
| 6,614,242 | B2 | 9/2003 | Matter et al. | 324/698 |
| 6,630,560 | B2 | 10/2003 | McGill et al. | 528/25 |
| 6,936,434 | B2 * | 8/2005 | McDonnell et al. | 435/31 |
| 2002/0144727 | A1 | 10/2002 | Kashkoush et al. | 137/93 |
| 2002/0168289 | A1 | 11/2002 | McVey | 422/28 |
| 2003/0063997 | A1 | 4/2003 | Fryer et al. | 422/3 |

OTHER PUBLICATIONS

U.S. Appl. No. 10/456,380, filed Jun. 6, 2003, Centanni, entitled: Method and Apparatus for Formulating and Controlling Chemical Concentrations in a Gas Mixture.

U.S. Appl. No. 10/667,988, filed Sep. 22, 2003, Korenev et al., entitled: Method and Apparatus for Measuring the Concentration of Hydrogen Peroxide in a Fluid.

T. J. Buckley et al., "*Toroidal Cross Capacitor for Measuring the Dielectric Constant of Gases,*" Review of Scientific Instruments, vol. 71, No. 7, Jul. 2000, pp. 2914-2921.

Gross et al., "*The Dielectric Constants of Water Hydrogen Peroxide and Hydrogen Peroxide-Water Mixtures,*" L. Amer. Chem. Soc., vol. 72, 1950, pp. 2075-2080.

"*Humidity Sensor Theory and Behavior,*" Psychometrics and Moisture, Honeywell HVAC, Nov. 27, 2002.

Philipp, "*Charge Transfer Sensing,*" 1997.

Wojslaw, "*Everything You Wanted to Know About Digitally Programmable Potentiometers,*" Catalyst Semiconductor, Inc., Oct. 17, 2001, Publication No. 6009.

Kittel, "*Introduction to Solid State Physics,*" Fourth Edition, John Wiley & Sons, Inc., 1971.

Philipp, "*The Charge Transfer Sensor,*" Sensors Magazine, Oct. 1999.

Steven J. Lasky, Howard R. Meyer & Daniel A. Buttry, Department of Chemistry, "Quartz Microbalance Studies of Solvent and Ion Transport in Thin Polymer Films in Sensor Applications of the QCH," *Technical Digest* 1990, pp. 1-4.

Sylvain Lazare and Vincent Granier, "Excimer Laser Light Induced Ablation and Reactions at Polymer Surfaces as Measured with a Quartz-Crystal Microbalance," Nov. 16, 1987, J. Appl. Phys 63 (6), Mar. 15, 1988, 1988 *American Institute of Physics*, pp. 2110-2115.

Stanley Bruckenstein, C. Paul Wilde, Michael Shay and A. Robert Hillman, "Experimental Observations on Transport Phenomena Accompanying Redox Switching in Polythionine Films Immersed in Strong Acid Solutions," 1990 American Chemical Society, pp. 787-793.

Robert R. McCaffrey, Stanley Bruckenstein and Paras N. Prasad, "Novel Application of the Quartz Crystal Microbalance to Study Langmuir-Blodgett Films," 1986 *American Chemical Society*, pp. 228-229.

J.A. Moore and Sang Youl Kim, "Diffusion of Small Molecules in Radiation Damaged PMMA Thin Films," 2002 Engineering Info. Inc., pp. 383-386.

Rade Ognjanovic, C.-Y. Hui, E.J. Kramer, "The Study of Polystyrene Surface Swelling Microbalance and Rutherford Backscattering Techniques," *Journal of Materials Science* 25 (1990), 1990 Chapman and Hall Ltd., pp. 514-518.

H.G. Tompkins, "Use of Surface and Thin Film Analysis Techniques to Study Metal-Organic and Metal-Polymer Interaction: A Review," *Thin Solid Films*, 119 (1984), pp. 337-348.

Sylvain Lazare, Jean Claude Soulignac and Pascal Fragnaud, "Direct and Accurate Measurement of Etch Rate of Polymer Films under Far-UV Irradiation," Appl. Phys. Lett. 50 (10), Mar. 9, 1987, 1987 American Institute of Physics, pp. 624-625.

Aljosa Vrhunec, Andreja Kolenc, Dusan Teslic, Iztok Livk and Ciril Pohar, "Crystal Size Distribution in Batch Sodium Perborate Precipitation,"*Acta Chim. Slov.* 1999, 46(4), pp. 543-554.

* cited by examiner

APPARATUS FOR CONTROLLING THE CONCENTRATION OF A STERILANT CHEMICAL IN A FLUID

RELATED APPLICATIONS

This application is a divisional of U.S. application Ser. No. 10/853,084, filed May 25, 2004.

FIELD OF THE INVENTION

The present invention relates generally to decontamination systems, and more particularly to a method and apparatus for controlling the concentration of a sterilant chemical in a fluid.

BACKGROUND OF THE INVENTION

Decontamination methods are used in a broad range of applications, and have used an equally broad range of sterilization agents. As used herein, the term "decontamination" refers to processes, including, but not limited to, "deactivation of biocontamination," "deactivation of chemical contamination," "sterilization," "disinfection" and "sanitization." Chemicals used to effect decontamination are interchangeably referred to herein as decontaminants or sterilants.

Decontamination systems rely on maintaining certain process parameters in order to achieve a target sterility or decontamination assurance level. For hydrogen peroxide vapor decontamination systems, those parameters include the concentration of liquid hydrogen peroxide in a liquid sterilant subject to vaporization, the concentration of the vaporized hydrogen peroxide in a vaporized sterilant, the degree of saturation, the temperature and pressure and the exposure time. By controlling these parameters, the desired sterility of decontamination assurance levels can be successfully obtained.

The present invention provides a method and apparatus for controlling the concentrations of a decontaminant or sterilant.

SUMMARY OF THE INVENTION

In accordance with a preferred embodiment of the present invention, there is provided a decontamination system comprising: (a) a first source of a first liquid sterilant including a sterilant chemical at a first concentration; (b) a second source of a second liquid sterilant including said sterilant chemical at a second concentration; (c) first regulating means for regulating a flow rate of the first liquid sterilant; (d) second regulating means for regulating a flow rate of the second liquid sterilant; (e) control means for controlling said first and second regulating means to produce a blended liquid sterilant comprised of the first and second liquid sterilant; (f) a vaporizer receiving said blended liquid sterilant to produce a vaporized sterilant; and (g) a chamber receiving said vaporized sterilant.

In accordance with another aspect of the present invention, there is provided a method for controlling a decontamination system having (a) a first source of a first liquid sterilant including a sterilant chemical at a first concentration, and (b) a second source of a second liquid sterilant including said sterilant chemical at a second concentration, the method comprising: (1) regulating a flow rate of the first liquid sterilant and of the second liquid to produce a blended liquid sterilant comprised of the first and second liquid sterilant; (2) vaporizing the blended liquid sterilant to produce a vaporized sterilant; and (3) introducing the vaporized sterilant into a treatment chamber.

Another advantage of the present invention is the provision of a method and apparatus for controlling chemical concentrations that allows the concentration of a sterilant chemical inside a sterilization chamber to be controlled within a desired concentration range.

Another advantage of the present invention is the provision of a method and apparatus for controlling chemical concentrations that allows an ideal concentration of sterilant chemical to be provided to a sterilization chamber.

An advantage of the present invention is the provision of a method and apparatus for controlling chemical concentrations that controls the concentration of a vaporized sterilant chemical in a treatment chamber by regulating the concentration of a liquid sterilant chemical prior to vaporization.

Another advantage of the present invention is the provision of a method and apparatus for controlling chemical concentrations that allows the concentration of a sterilant chemical inside a sterilization chamber to be controlled to compensate for the half life and absorption associated with the sterilant chemical.

These and other objects will become apparent from the following description of a preferred embodiment taken together with the accompanying drawings and the appended claims.

BRIEF DESCRIPTION OF THE DRAWINGS

The invention may take physical form in certain parts and arrangement of parts, a preferred embodiment of which will be described in detail in the specification and illustrated in the accompanying drawings which form a part hereof, and wherein.

DETAILED DESCRIPTION OF PREFERRED EMBODIMENT

Figure 1:
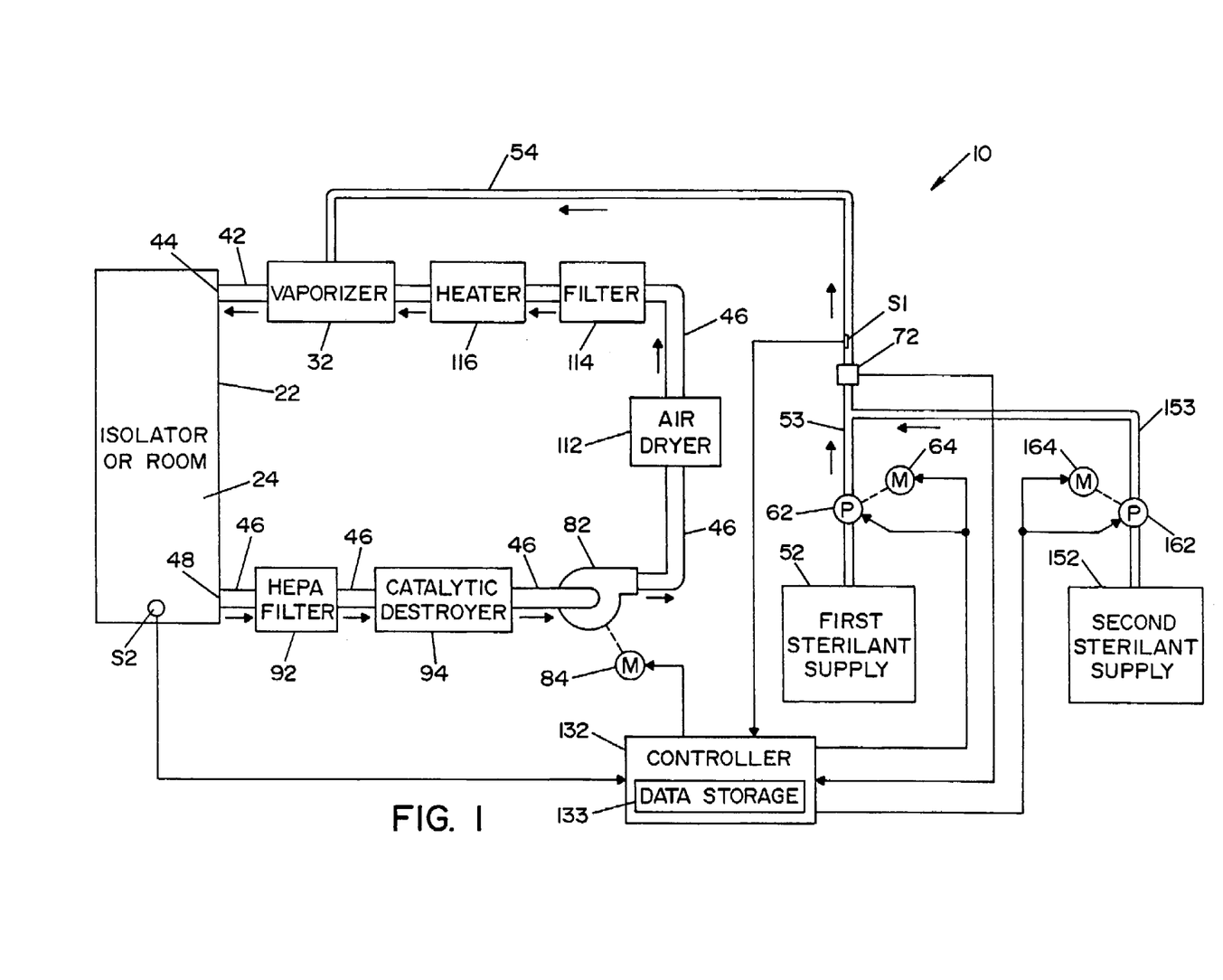
FIG. 1 is a schematic view of a decontamination system.

Referring now to the drawings wherein the showings are for the purpose of illustrating a preferred embodiment of the invention only, and not for the purpose of limiting same, FIG. 1 shows a decontamination system 10 having sensors S1 and S2 for determining the concentration of a sterilant chemical used within system 10. In the embodiment shown, system 10 is a closed-loop decontamination system for decontaminating objects with hydrogen peroxide, and more particularly, with vaporized hydrogen peroxide. It should be understood that the present invention is also suitable for use in connection with open loop decontamination systems.

Sensor S1 shall be described with respect to determining the concentration of liquid hydrogen peroxide in a multi-component liquid sterilant. Sensor S2 shall be described with respect to determining the concentration of vaporized hydrogen peroxide in a multi-component, vapor-phase sterilant. It will of course be appreciated that sensors S1 and S2 according to the present invention may find advantageous application in determining the concentration of sterilant chemicals other than hydrogen peroxide.

In the embodiment shown, system 10 includes an isolator or room 22 that defines an inner treatment chamber 24. It should be understood that treatment chamber 24 may take the form of a region. It is contemplated that articles to be decontaminated may be disposed within isolator or room 22. A vaporizer (also referred to as generator) 32 is connected to chamber 24 of isolator or room 22 by means of a supply conduit 42. Supply conduit 42 defines an inlet 44 to chamber 24. Vaporizer 32 is connected to a first liquid sterilant supply 52 and a second liquid sterilant supply 152 by a feed line 54 and supply feed lines 53 and 153. Liquid sterilant received by vaporizer 32 is vaporized by conventionally known means.

A pump 62 driven by a motor 64 is provided to convey metered amounts of a liquid sterilant from first liquid sterilant supply 52 to vaporizer 32. Similarly, a pump 162 driven by a motor 164 is provided to convey metered amounts of a liquid sterilant from second liquid sterilant supply 152 to vaporizer 32. In a preferred embodiment, pumps 62 and 162 are electronically-controlled metering pumps. Conventional metering pumps transfer fluid in two stages, namely, an intake stroke and an output stroke. During the intake stroke, fluid is pulled into a pump cavity past an inlet check valve. During the output stroke, the inlet valve closes, an outlet valve opens, and the fluid is forced out. The flow may be varied by changing the stroke length or by adjusting the cycle frequency. The pump flow rate is electronically controlled.

Through control of the operation of pumps 62 and 162, the flow rate of liquid sterilant received by vaporizer 32 from each of the first and second liquid sterilant supplies 52 and 152 can be selectively regulated, as will be described in detail below. It should be appreciated that system 10 may include other devices for regulating the flow of liquid sterilant from first and second liquid sterilant supplies 52 and 152, including, but not limited to valves, flowmeters, and the like.

A pressure switch 72 is provided in feed line 54. Pressure switch 72 is operable to provide an electrical signal in the event that a certain static head pressure does not exist in feed line 54.

Isolator or room 22 and vaporizer 32 are part of a closed loop system that includes a return conduit 46 that connects an outlet port 48 to isolator or room 22 (and chamber 24) to vaporizer 32. A blower 82, driven by a motor 84, is disposed within return conduit 46 between isolator or room 22 and vaporizer 32. Blower 82 is operable to circulate sterilant and a carrier gas, preferably air, through the closed loop system. A first filter 92 and catalytic destroyer 94 are disposed in return conduit 46 between blower 82 and isolator or room 22, as illustrated in FIG. 1. First filter 92 is preferably a HEPA filter and is provided to remove contaminants flowing through system 10. Catalytic destroyer 94 is operable to destroy vaporized hydrogen peroxide ($H_2O_2$) flowing therethrough, as is conventionally known. Catalytic destroyer 94 converts the vaporized hydrogen peroxide ($H_2O_2$) into water and oxygen. An air dryer 112, a second filter 114 and a heater 116 are disposed within return line 46 between blower 82 and vaporizer 32. Air dryer 112 is operable to remove moisture from air blown through the closed loop system. Second filter 114 is operable to filter the air blown through return conduit 46 by blower 82. Heater 116 is operable to heat air blown through return conduit 46 by blower 82. In this respect, air is heated prior to the air entering vaporizer 32.

Controller 132 is a system microprocessor or microcontroller programmed to control the operation of system 10. As illustrated in FIG. 1, controller 132 is also electrically connected to motors 64, 84, and 164, and to pumps 62 and 162. Controller 132 also preferably includes (or is connected with) a data storage device 133 for storing data.

Sensors S1 and S2 may take the form of any sensor suitable for determining the concentration of sterilant chemicals used within system 10. Sensor S1 is preferably disposed within feed line 54 to sense the concentration of liquid hydrogen peroxide therein. Similarly, sensor S2 is preferably disposed within chamber 24 to sense the concentration of vapor-phase hydrogen peroxide therein. Exemplary sensors S1 and S2 will now be described in detail. In accordance with the present invention, it is contemplated that system 10 may be configured with only sensor S1, only sensor S2, or sensors S1 and S2 in combination. Furthermore, it should be appreciated that in an alternative embodiment additional sensors could be located in either or both feed lines 53 and 153, or inside first and second sterilant supplies 52 and 152, to determine the concentration of the liquid hydrogen peroxide therein.

Figure 2:
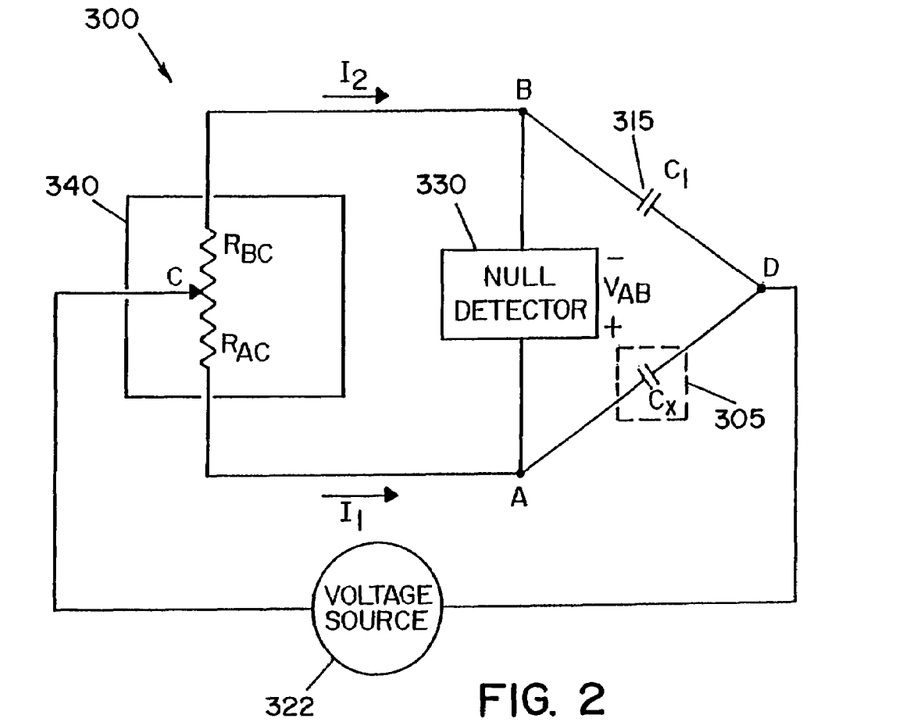
FIG. 2 is a schematic diagram of an exemplary capacitive sensor for determining the concentration of a sterilant chemical used in a decontamination system, according to a first embodiment.

An exemplary sensor S1 is sensor 300, shown in FIG. 2. Sensor 300 is described in detail in U.S. patent application Ser. No. 10/389,036, filed Mar. 14, 2003, entitled "Method and Apparatus for Measuring Chemical Concentration in a Fluid," and is fully incorporated herein in its entirety.

Broadly stated, sensor 300 includes a capacitor 305 that acts as a sensing element. Electrical properties of capacitor 305 are responsive to a sterilant chemical used in system 10. In this regard, it should be appreciated that the dielectric constant of a capacitor is dependent on electronic "polarizability." Polarization is the ability of molecules to form a dipole under an electric field or the ability of the electric field to line up or rotate an inherent dipole, such as water molecules.

According to the embodiment illustrated in FIG. 2, sensor 300 takes the form of a "bridge circuit." As is well known to those skilled in the art, bridge circuits are used to determine the value of an unknown impedance in terms of other impedances of known value. Highly accurate measurements are possible because a null condition is used to determine the unknown impedance. The bridge circuit is used to determine a capacitance value indicative of the concentration of a sterilant chemical used in system 10.

Sensor 300 is generally comprised of a voltage source 322, a null detector 330, an electronic potentiometer 340, a capacitor 315 of a known capacitance $C_1$, and capacitor 305 having a capacitance $C_x$.

Capacitor 305 is directly exposed to liquid sterilant flowing through feed line 54. The liquid sterilant fills the gap between the conducting plates of capacitor 305, thereby acting as the insulator or "dielectric" of capacitor 305. Capacitance $C_x$ of capacitor 305 will vary in accordance with the concentration of the sterilant chemical in the liquid sterilant.

In a preferred embodiment, capacitor 305 is a parallel plate capacitor. However, it should be appreciated that capacitor 305 could be constructed in a different form. For example, capacitor 305 could be a cylindrical or spherical capacitor. If a spherical capacitor is used as capacitor 305, holes must be placed in the outer shell of capacitor 305 such that the liquid sterilant can enter and exit the capacitor.

Electronic potentiometer 340 functions in the same manner as a mechanical potentiometer. In this regard, electronic potentiometer 340 is a three terminal device. Between two of the terminals is a resistive element. The third terminal known as the "wiper" is connected to various points along the resistive element. In the illustrated embodiment, the wiper is digitally controlled by controller 132 (see FIG. 1). The wiper divides the resistive element into two resistors $R_{BC}$ and $R_{AC}$. Electronic potentiometer 340 may take the form of a digitally programmable potentiometer (DPP™) available from Catalyst Semiconductor, Inc. of Sunnyvale, Calif.

In a preferred embodiment, voltage source 322 provides an AC voltage signal, such as a sinusoidal or pulse waveform. Null detector 330 is a device for detecting a null condition (i.e., a short circuit), such as a galvanometer, a voltmeter, a frequency-selective amplifier, and the like.

Operation of sensor 300 will now be described in detail. The elements of the bridge circuit are connected between junctions AC, BC, AD, and BD. Electronic potentiometer 340 is operated by controller 132 to vary the resistances $R_{BC}$ and $R_{AC}$ until the potential difference between junctions A and B ($V_{AB}$) is zero. When this situation exists, the bridge is said to be balanced or is "nulled." The following relationships then hold for voltages in the main branches:

$$V_{AC} = V_{BC}, \text{ and } V_{AD} = V_{BD},$$

where $V_{AC}$ is the voltage between junctions A and C, $V_{BC}$ is the voltage between junctions B and C, $V_{AD}$ is the voltage between junctions A and D, and $V_{BD}$ is the voltage between junctions B and D. Accordingly, $$V_{AD}/V_{AC} = V_{BD}/V_{BC}$$

$$V_{AD} = V_{BD}/(V_{AC}/V_{BC})$$

Capacitor 305 of capacitance $C_x$ is connected between junctions A and D, and capacitor 315 of known capacitance $C_1$ is connected between junctions B and D. Electronic potentiometer 340, connected from junction A to junction C to junction B, is adjusted by controller 132 to vary the voltages $V_{AC}$ and $V_{BC}$.

When a null is detected by null detector 330, current $I_1$ flows from junction C to junction A to junction D, and a current $I_2$ flows from junction C to junction B to junction D. The voltage $V_{AC}$ across junctions A to C, and the voltage $V_{BC}$ across junctions B to C are:

$$V_{AC} = I_1 R_{AC} \text{ and } V_{BC} = I_2 R_{BC}.$$

The voltage across a capacitor with capacitance C, current I, and frequency is:

$$V = \frac{I}{2\pi f C}$$

Therefore, the voltages $V_{AD}$ and $V_{BD}$ may be expressed as:

$$V_{AD} = \frac{I_1}{2\pi f C_x} \quad V_{BD} = \frac{I_2}{2\pi f C_1}$$

As discussed above, $V_{AD} = V_{BD}/(V_{AC}/V_{BC})$, $V_{AC} = I_1 R_{AC}$, and $V_{BC} = I_2 R_{BC}$. Therefore, $$C_x = C_1 \left( \frac{R_{BC}}{R_{AC}} \right).$$

In view of the forgoing relationship, when a null condition is detected, the resistance values for $R_{BC}$ and $R_{AC}$, along with the known capacitance $C_1$ of capacitor 315, can be used to determine the unknown value of capacitance $C_x$ of capacitor 305.

Differences in dipole moments of different molecules are used to determine the concentration of liquid hydrogen peroxide in fluid line 54. As discussed above, liquid sterilant fills the gap between the conducting plates of capacitor 305, thereby acting as the dielectric of capacitor 305. By configuring capacitor 305 as an element of a bridge circuit, a measure of resistance values $R_{AC}$ and $R_{BC}$, when the bridge is balanced or nulled, can be used to determine the capacitance $C_x$ of capacitor 305. The capacitance $C_x$ of capacitor 305 is indicative of the concentration of the hydrogen peroxide in fluid line 54, since the permittivity of the respective dielectric is affected by the relative concentration of hydrogen peroxide in the liquid sterilant.

It is well known that for a parallel plate capacitor $C = (k \in_0)(A/d) = (\in)(A/d)$, where C is capacitance, k is the dielectric constant, $\in_0$ is the permittivity of free space ($8.85 \times 10^{-12}$ F/m), $\in$ is the permittivity (Farads/meter) of the capacitor dielectric, A is the area of the capacitor plates (m²), and d is the separation in meters between the capacitor plates. As $\in$ increases, the capacitance C will increase. Where the capacitor is a parallel plate capacitor with circular plates of diameter D, $C = (\pi D^2 \in)/(4d)$.

It will be appreciated that the dielectric constant k of the capacitor can be determined according to the following expression:

$$k = \frac{4dC}{\pi D^2 \varepsilon_0},$$

where the value of capacitance, C, is determined as discussed above. The dielectric constant of the capacitor can also be determined by determining the capacitance with the dielectric in place between the conducting plates ($C_d$), and then determine the capacitance without the dielectric in place ($C_o$). The ratio of the two capacitances equals the dielectric constant, $$k = \frac{C_d}{C_0}.$$

The response of a capacitor is influenced by the characteristics (e.g., frequency) of the AC waveform applied thereto. In this regard, capacitive reactance ($X_c$) is a function of frequency. Capacitive reactance is the opposition offered to the flow of alternating current by pure capacitance, and is expressed in ohms ($X_c = 1/(2\pi f C)$). Accordingly, frequency of the waveform generated by voltage source 322 influences the response of capacitors. Thus, the frequency selected for voltage source 322 should preferably be a frequency that will provide a generally linear response for capacitance as the concentration of a sterilant chemical is varied. This will facilitate the use of interpolation and extrapolation of capacitance values, as will be discussed further below. If a suitable linear response is not obtained, then an expanded set of data points should be stored in data storage device 133.

Figure 3:
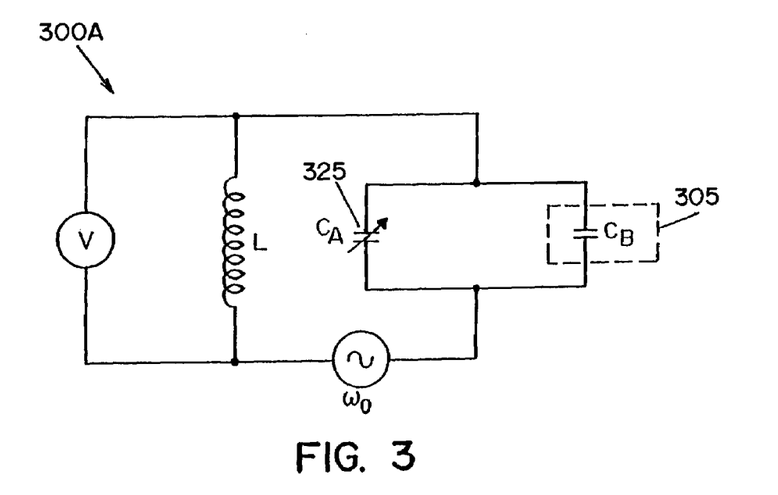
FIG. 3 is a schematic diagram illustrating an exemplary capacitive sensor for determining the concentration of a sterilant chemical used in a decontamination system, according to a second embodiment.

It should be appreciated that while a preferred embodiment of the present invention includes a sensor 300 in the form of a bridge circuit, other types of circuits and techniques (including other types of bridge circuits, and capacitance meters)

known to those skilled in the art, may be suitably used to measure capacitance. For example, FIG. 3 illustrates an alternative sensor 300A. Sensor 300A is an LC resonant circuit, including a variable capacitor 325 (having a capacitance $C_A$), and capacitor 305 (having a capacitance $C_x$) that acts as the sensing element, as described above. Since the resonance frequency $\omega_0 = [L(C_A + C_x)]^{-1/2}$, the unknown capacitance $C_x$ of capacitor 305 can be determined.

Figure 4:
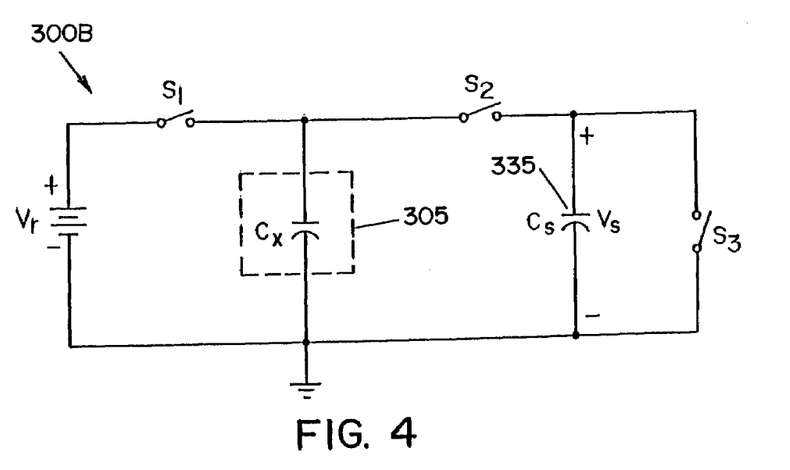
FIG. 4 is a schematic diagram illustrating an exemplary capacitive sensor for determining the concentration of a sterilant chemical used in a decontamination system, according to a third embodiment.

FIG. 4 illustrates yet another alternative sensor 300B suitable for use in connection with the present invention. Sensor 300B is a "charge transfer" sensor circuit. Charge transfer sensor circuits are recognized to provide resolutions of fractions of a femtoFarad. In a charge transfer sensor circuit the unknown capacitance $C_x$ of a sense electrode is determined by charging the sense electrode to a fixed potential, and then transferring that charge to a charge detector comprising a capacitor 335 of known capacitance $C_s$. In sensor 300B, capacitor 305 of unknown capacitance $C_x$ acts as a sensing element, as described above. In this regard, liquid sterilant in fluid line 54 fills the gap between the conducting plates of capacitor 305, thereby acting as an insulator or "dielectric" of capacitor 305. Capacitor 305 is first connected to a DC reference voltage ($V_r$) via a switch $S_1$. Switch $S_1$ is reopened after capacitor 305 is satisfactorily charged to the potential of $V_r$. Then, after as brief as possible a delay so as to minimize leakage effects caused by conductance, switch $S_2$ is closed and the charge (Q) present on capacitor 305 is transferred to capacitor 335 (i.e., the charge detector). Once the charge Q is satisfactorily transferred to capacitor 335, switch $S_2$ is reopened. By reading voltage $V_s$, the capacitance $C_x$ of capacitor 305 can be determined. $V_s$ may be input to an amplifier to provide the scaling necessary to present an analog-to-digital converter (ADC) with a useful range of voltage for digital processing. Switch $S_3$ acts as a reset means to reset the charge between charge transfer cycles, so that each charge transfer cycle has a consistent initial condition. Switches $S_1$, $S_2$ and $S_3$ may be electromechanical switches or transistors. Preferably, digital control logic is used to control switches $S_1$, $S_2$ and $S_3$. In a preferred embodiment, capacitor 335 is selected to be significantly larger than capacitor 305.

The equations governing sensor 300B are as follows:

$$V_s = V_r[C_y/(C_y + C_s)], \text{ therefore}$$

$$C_y = V_s C_s/[V_r - V_s].$$

The charge-transfer sensor has been applied in a self-contained capacitance-to-digital-converter (CDC) integrated circuit (IC). For example, Quantum Research Group produces a QProx™ CDC sensor IC (e.g., QT300 and QT301 CDC sensor ICs) for detecting femtofarad level changes in capacitance. The CDC sensor IC outputs a digital value corresponding to the detected input capacitance. The value of an external sampling capacitor controls the gain of the sensor.

Other high sensitivity circuitry is provided by such devices as the PTL 110 capacitance transducer from Process Tomography Limited of Cheshire, United Kingdom. The PTL 110 measures small values of capacitance (up to 10 picoFarads) with a resolution of 1 femtoFarad. A 1616 Precision Capacitance Bridge from IET Labs, Inc. of Westbury, N.Y., allows for measurement of capacitances in the range from 10-7 pF to 10 μF. Tektronix produces the Tektronix 130 LC Meter that measures capacitance from 0.3 pF to 3 pF. It has also been acknowledged in the prior art literature that capacitance sensor circuits using modern operational amplifiers and analog-to-digital converters (ADCs) can easily obtain resolutions to 0.01 pF.

Referring now to FIG. 2, determination of the concentration of liquid hydrogen peroxide in feed line 54 using capacitor 305 of capacitance $C_x$ will now be described in connection with sensor 300.

Capacitor 305 is exposed to known concentrations of liquid hydrogen peroxide in an aqueous solution to develop a set of data, or a curve, of capacitance values $C_x$ as a function of concentration of liquid hydrogen peroxide in the aqueous solution. The associated set of data, or curve, is programmed or stored in data storage device 133 of controller 132. As the concentration of the liquid hydrogen peroxide is varied, the corresponding capacitance $C_x$ of capacitor 305 is determined, and stored in data storage device 133. For instance, capacitance of capacitor $C_x$ may be determined for various concentrations of an aqueous solution of hydrogen peroxide comprised of liquid hydrogen peroxide and water (at a fixed volume of the aqueous solution), including, but not limited to:

0% liquid hydrogen peroxide and 100% water,
25% liquid hydrogen peroxide and 75% water,
50% liquid hydrogen peroxide and 50% water,
75% liquid hydrogen peroxide and 25% water, and
100% liquid hydrogen peroxide and 0% water.

After the set of data is stored in data storage device 133, measurement of the concentration of the liquid hydrogen peroxide can commence. Capacitor 305 is exposed to an aqueous solution of hydrogen peroxide. A determination of $R_{AC}$ and $R_{BC}$ when the bridge is nulled is then used to determine a value for the capacitance $C_x$ of capacitor 305. As discussed above, $C_x = C_1(R_{BC}/R_{AC})$. The data stored in data storage device 133 is searched for the measured capacitance value $C_x$ to obtain the corresponding concentration of hydrogen peroxide.

A linear relationship between concentration and capacitance allows one to normalize any measurement made so as to provide the absolute concentration of the hydrogen peroxide. If the measured capacitance $C_x$ of capacitor 305 is not found in the pre-stored data, the stored data may be interpolated or extrapolated to obtain a concentration corresponding to the measure capacitance $C_x$ of capacitor 305. As noted above, frequency of the waveform generated by voltage source 322 will influence the response of capacitors. Where the capacitance $C_x$ of capacitor 305 does not exhibit a suitable linear response, an expanded set of data points should be stored in data storage device 133, so that interpolation or extrapolation is unnecessary.

It should be appreciated that while a preferred embodiment of the present invention uses a measure of a capacitor's capacitance to determine concentration, it is also contemplated that a measure of other electrical properties associated with a capacitor may be used to determine concentration, including, but not limited to, the permittivity and dielectric constant of the capacitor dielectric.

Figure 5:
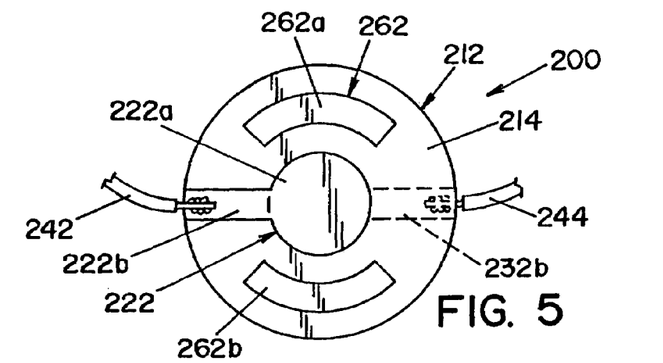
FIG. 5 is a top, plan view of an exemplary piezoelectric sensor for determining the concentration of a sterilant chemical used in a decontamination system.
Figure 6:
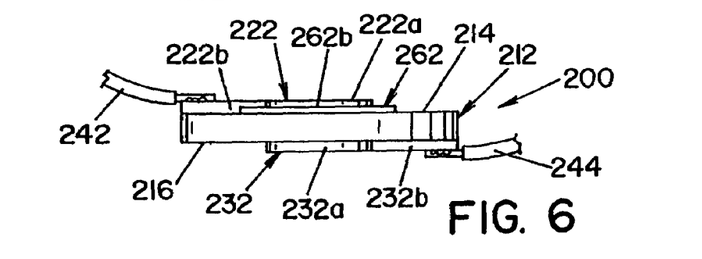
FIG. 6 is a side, elevation view of the sensor shown in FIG. 5.
Figure 7:
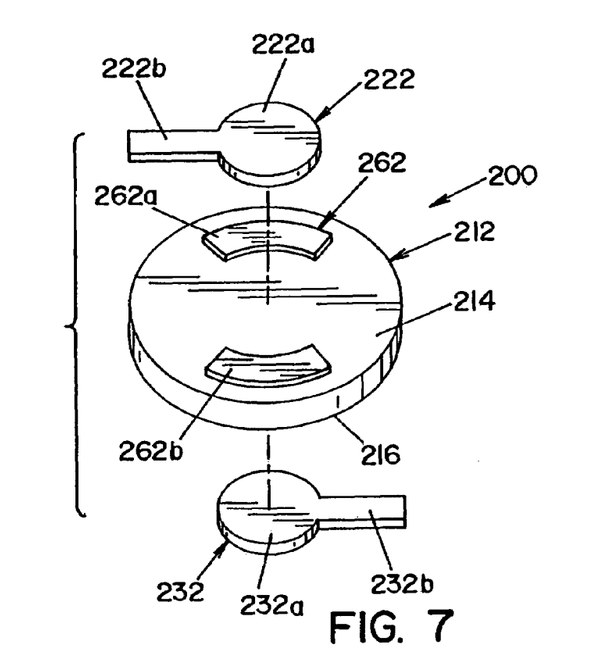
FIG. 7 is an exploded view of the sensor shown in FIG. 5.

An exemplary sensor S2 is sensor 200, as shown in FIGS. 5-7. Sensor 200 is described in detail in U.S. patent application Ser. No. 10/663,593, filed Sep. 16, 2003, entitled "Sensor for Determining Concentration of Fluid Sterilant," and is fully incorporated herein in its entirety.

Broadly stated, sensor 200 is comprised of an element 212 having a layer or coating 262 of a material that interacts with, or is reactive with, a sterilant chemical used in system 10, such that mechanical motion or movement of element 212 is converted into an electrical signal.

Element 212 may be a moving or suspended component, but in a preferred embodiment, element 212 is a piezoelectric device, and more preferably, is a quartz crystal. Other piezoelectric materials, such as by way of example and not limitation, Rochelle salt, barium titanate, tourmaline, polyvinylidene fluoride and crystals that lack a center of symmetry are also contemplated. In the embodiment shown, element 212 is a flat, circular quartz disk having a first planar, major surface 214 and a second planar, major surface 216. An electrode 222 is disposed on the first major surface 214 and an electrode 232 is disposed optionally on the second major surface 216.

Electrode 222 includes a main body portion 222a that is centrally disposed on first major surface 214 and a leg portion 222b that extends in a first direction to the edge of element 212. Similarly, electrode 232 includes a main body portion 232a that is centrally disposed on second major planar surface 216, and a leg portion 232b that extends in a direction opposite to the first direction of leg portion 222b, wherein leg portion 232b extends to the edge of element 212. Main body portions 222a, 232a of electrodes 222, 232 are disposed respectively on first and second major surfaces 214, 216 to be aligned with each other on opposite sides of element 212. Leg portions 222b, 232b extend in opposite directions from central body portions 222a, 232a, as best seen in the drawings. Electrodes 222, 232 are deposited onto first and second planar surfaces 214, 216. Electrodes 222, 232 may be formed of any electrically conductive material, but are preferably formed of copper, silver or gold. Electrical leads 242, 244 are attached to leg portions 222b, 232b of electrodes 222, 232. Leads 242, 244 are soldered, brazed or welded to electrodes 222, 232 to be in electrical contact therewith.

At least one of the two major surfaces 214, 216 of element 212 is coated with a layer 262 of a material that interacts, or is reactive with, the sterilant chemical used within system 10. In the embodiment shown, layer 262 is on major surface 214. In the embodiment shown, layer 262 is defined by two arcuate or crescent-shaped layer areas 262a, 262b of material applied to first major surface 214 of element 212. Arcuate layer areas 262a, 262b are disposed on first major surface 214 such that electrode 222 is disposed therebetween. The material forming layer areas 262a, 262b are preferably fixedly attached to surface 214 of element 212. As will be appreciated from a further description of the present invention, the mass of the material on element 212 is dependent upon the desired performance characteristics of sensor 200. As indicated above, the material forming layer areas 262a, 262b are preferably one that interacts or reacts with the sterilant chemical used within system 10.

In the illustrated embodiment of the present invention, the sterilant chemical to be detected by sensor 200 is vaporized hydrogen peroxide, and the material that forms layer areas 262a, 262b on first major surface 214 of sensor 200 is a metal oxide, namely, lead dioxide ($PbO_2$). It is believed that other metal oxides having various states, such as silver (II) oxide (AgO) or manganese (IV) oxide ($MnO_2$), may be used. It is also contemplated that metal oxides having mixed valency states, such as by way of example and not limitation, a metal oxide having a mixture of single and divalent oxide states may be used.

Layer areas 262a, 262b are preferably formed by a thin film deposition process. It should be understood that the term "thin film deposition" is inclusive of Physical Vapor Deposition (PVD) and Chemical Vapor Deposition (CVD). PVD is used in accordance with a preferred embodiment of the present invention. PVD includes the processes of evaporation, ion-beam assisted electron beam deposition, and "sputtering" (which includes ion beam deposition).

Evaporation includes processes such as electron beam evaporation (also referred to herein as "electron beam deposition"), as well as processes wherein a material is heated inside a vacuum chamber by a heater to form a vapor, without use of an electron beam. The heating is classified as (a) resistive or (b) inductive. The evaporation processes which do not use an electron beam are commonly used to deposit $SiO_2$ or SiO thin films, and can also be used in conjunction with an ion-beam assist. Ion-beam assisted evaporation (with and without use of an e-beam) are collectively referred to herein as "ion-beam assisted deposition."

Sputtering refers to a glow discharge process whereby bombardment of a cathode releases atoms from the surface which then deposit onto a nearby surface to form a coating. For example, sputtering occurs when energetic ionized particles impinge on the surface of a target material, causing the emission of particles and erosion of the surface of a solid. This particular sputtering process is also referred to herein as "ion beam deposition."

In the illustrated embodiment, sensor 200 is disposed within chamber 24, as sensor S2 and is connected to system controller 132 to provide electrical signals therebetween (FIG. 1). Controller 132 includes an oscillating circuit (not shown) that is connected to sensor 200 to convert movement of sensor 200 into electrical signals, as is conventionally known. Data storage device 133 of controller 132 stores data indicative of the electrical responses of sensor 200 to predetermined concentrations of a sterilant chemical to be sensed. In the embodiment heretofore described, where element 212 is a quartz crystal and layer areas 262a, 262b are lead dioxide, the data relating to sensor 200 that is stored within data storage device 133 is empirical data accumulated under controlled, laboratory conditions.

The empirical data relating to sensor 200 that is stored in data storage device 133 may be acquired as follows. The natural frequency of a quartz crystal (without a coating thereon) is measured. The lead dioxide is applied to the quartz crystal and the mass of the coating is determined using the Sauerbre equation. The quartz crystal is then exposed to various, controlled concentrations of vaporized hydrogen peroxide. A graph of the change in frequency per unit mass of coating (or, using the Sauerbre equation, the change in weight per unit mass of coating) versus concentration of sterilant chemical is produced and stored in a data storage device within controller 132. Alternatively, the data could be stored not as a graph but rather in look up tables. As will be appreciated, if a coating of uniform thickness is applied to a crystal, the change in frequency or weight could be normalized on a per unit surface area basis.

As suggested, in one embodiment, the change in frequency or weight is divided by the mass of the coating applied to the quartz crystal so that regardless of the mass of coatings applied to other crystals, the change in frequency will be normalized to a unit mass of the coating. Data taken with other quartz crystals that may have coatings of different amounts of mass than the laboratory crystal can still be compared to the stored data obtained from the laboratory crystal as both sets of data will be normalized to a change in frequency or weight per unit mass of the coating. It will be appreciated that with modern deposition means, it may not be necessary to normalize the data as coatings with little physical variation can be deposited from one crystal to the next.

In another embodiment, a quartz crystal is coated with lead oxide and is then exposed to known concentrations of vaporized hydrogen peroxide so as to develop a set of data, or a curve, of equilibrium frequency reduction values as a function of concentration of vaporized hydrogen peroxide for the quartz crystal. The coated quartz crystal is then installed in a system 10. The associated set of data, or curve, is programmed or stored in controller 132 of the system 10. Thus, the data stored in the system 10 matches the crystal sensor within the system 10, thereby providing a standardized system. In this manner, each system 10 has a coated quartz crystal sensor with an associated standardized data set therein, as the stored data set was produced by exposing that specific quartz crystal to known concentrations of vaporized hydrogen peroxide.

Sensor 200 operates based upon the concept that the frequency of a piezoelectric device will change in relation to a change in mass of a layer on the device, as a result of exposure to vaporized hydrogen peroxide.

Specifically, the frequency of a piezoelectric device is related to the mass change, as determined by the Sauerbre equation:

$$\Delta f = -(C_f)(\Delta m)$$

$$\Delta f = -(f_o^2/N\rho)\Delta m$$

where:
- $\Delta f$ is the frequency change
- $\Delta m$ is the mass change per unit area on the surface of the piezoelectric device
- $C_f$ is a sensitivity constant
- $f_o$ is the operating frequency of the piezoelectric device prior to the mass change
- N is the frequency constant for the piezoelectric device
- $\rho$ is the density of the piezoelectric device It should be appreciated that use of other electrical/mechanical devices that support a material sensitive to vaporized hydrogen peroxide as discussed herein are also contemplated. In such a case, a change in the physical properties of the electrical/mechanical device as it is exposed to vaporized hydrogen peroxide is correlated to a change in the concentration of the vaporized hydrogen peroxide.

The present invention shall now be further described with reference to the operation of system 10 (FIG. 1). A typical decontamination cycle includes a drying phase, a conditioning phase, a decontamination phase and an aeration phase.

Isolator or room 22, supply conduit 42 and return conduit 46 define a closed loop conduit circuit. When a decontamination cycle is first initiated, controller 132 causes blower motor 84 to drive blower 82, thereby causing a carrier gas to circulate through the closed loop circuit. In the embodiment shown, the carrier gas is air. During a drying phase, vaporizer 32 is not operating. Air dryer 112 removes moisture from the air circulating through the closed loop system, i.e., through supply conduit 42, return conduit 46 and chamber 24 or isolator or room 22, as illustrated by the arrows in FIG. 1. When the air has been dried to a sufficiently low humidity level, the drying phase is complete.

The conditioning phase is then initiated by activating vaporizer 32 and sterilant supply motors 64, 164 to provide liquid sterilant to vaporizer 32. In accordance with a preferred embodiment of the present invention, the concentration of hydrogen peroxide in the liquid sterilant supplied from first sterilant supply 52 is different from the concentration of hydrogen peroxide in the liquid sterilant supplied from second sterilant supply 152.

By way of example, and not limitation, the liquid sterilant supplied from first sterilant supply 52 may be comprised of about 35% hydrogen peroxide (by weight) and about 65% water (by weight), whereas the liquid sterilant supplied from second sterilant supply 152 may be comprised of about 50% hydrogen peroxide (by weight) and about 50% water (by weight). It should be understood that liquid sterilants comprised of different ratios of hydrogen peroxide and water are also contemplated. For example, liquid sterilant from first sterilant supply 52 may be comprised of 90% to 100% hydrogen peroxide (by weight) and 0% to 10% water (by weight) and the liquid sterilant from second sterilant supply 152 may be comprised of 90% to 100% water (by weight). In the case of aqueous hydrogen peroxide, the liquid hydrogen peroxide is preferably in a range of about 25% to 75% (by weight) of the liquid sterilant.

The flow rate of pumps 62 and 162 is controlled by controller 132 to blend liquid sterilant from first sterilant supply 52 and second sterilant supply 152, thereby producing a blended liquid sterilant having a desired concentration of liquid hydrogen peroxide. In this regard, pumps 62 and 162 can supply vaporizer 32 with liquid sterilant having a hydrogen peroxide concentration that ranges from the hydrogen peroxide concentration of the liquid sterilant of first sterilant supply 52 to the hydrogen peroxide concentration of the liquid sterilant of second sterilant supply 152.

To provide vaporizer 32 with liquid sterilant having a hydrogen peroxide concentration of the liquid sterilant of first sterilant supply 52, controller 132 reduces the flow rate of pump 162 to zero, and allows only liquid sterilant from first sterilant supply 52 to pass into feed line 54. Likewise, to provide vaporizer 32 with liquid sterilant having a hydrogen peroxide concentration of the liquid sterilant of second sterilant supply 152, controller 132 reduces the flow rate of pump 62 to zero, and allows only liquid sterilant from second sterilant supply 152 to pass into feed line 54.

To provide vaporizer 32 with liquid sterilant having a hydrogen peroxide concentration that is between: (a) the concentration of hydrogen peroxide of the liquid sterilant of first sterilant supply 52 and (b) the concentration of hydrogen peroxide of the liquid sterilant of second sterilant supply 152, controller 132 controls the flow rate of pumps 62 and 162 to allow both sterilant supply 52 and sterilant supply 152 to supply liquid sterilant to feed line 54.

Sensor S1 supplies controller 132 with data indicating the concentration of hydrogen peroxide in the liquid sterilant flowing inside feed line 54. In response to the data supplied by sensor S1, controller 132 controls pumps 62 and 162 to modify the respective flow rates. Accordingly, a blended liquid sterilant can be produced that has the desired concentration of hydrogen peroxide. The desired concentration of the liquid hydrogen peroxide may be a function of the concentration of vapor-phase hydrogen peroxide sensed by sensor S2 inside chamber 24. It should be appreciated that controller 132 may also control pumps 62 and 162 in response to data supplied by sensor S2.

Within vaporizer 32, the liquid sterilant is vaporized to produce vaporized hydrogen peroxide and water vapor, in a conventionally known manner. The vaporized sterilant is introduced into the closed loop conduit circuit and is conveyed through supply conduit 42 by the carrier gas (air) into chamber 24 within isolator or room 22. During the conditioning phase, vaporized hydrogen peroxide is injected into chamber 24 at a relatively high rate to bring the hydrogen peroxide level up to a desired level in a short period of time. During the conditioning phase, blower 82 causes air to continuously circulate through the closed loop system. As vaporized hydrogen peroxide enters chamber 24 from vaporizer 32, vaporized hydrogen peroxide is also being drawn out of chamber 24 through catalytic destroyer 94 where it is broken down into water and oxygen.

After the conditioning phase is completed, the decontamination phase is initiated. During the decontamination phase, the liquid sterilant injection rate to vaporizer 32 and to chamber 24 is decreased to maintain the hydrogen peroxide concentration constant at a desired level. The decontamination phase is run for a predetermined period of time, preferably with the hydrogen peroxide concentration remaining constant at a desired level, for a predetermined period of time that is sufficient to effect the desired decontamination inside chamber 24.

After the decontamination phase is completed, controller 132 causes vaporizer 32 to shut down, thereby shutting off the flow of vaporized hydrogen peroxide into chamber 24.

Thereafter, the aeration phase is run to bring the hydrogen peroxide level down to an allowable threshold (about 1 ppm). In this respect, as will be appreciated, blower 82 continues to circulate the air and sterilant through the closed loop system, thereby causing the last of the vaporized hydrogen peroxide to be broken down by catalytic destroyer 94.

Sensor 200 is exposed to the atmosphere within chamber 24. During the aeration phase of system 10, an operating frequency $f_o$ of sensor 200 is determined by controller 132. Operating frequency $f_o$ is essentially a baseline frequency of sensor 200 prior to any mass change that would be the result of exposure of sensor 200 to the vaporized hydrogen peroxide. During the conditioning phase, sensor 200 is exposed to the vaporized hydrogen peroxide entering chamber 24. The hydrogen peroxide ($H_2O_2$) produces a reaction with the lead dioxide ($PbO_2$). It is believed that the following reaction occurs:

$$PbO_2 + H_2O_2 \leftrightarrows PbO_2 + H_2O + (\tfrac{1}{2})O_2$$

The reaction between the lead dioxide ($PbO_2$) of layer areas 262a, 262b and the hydrogen peroxide ($H_2O_2$) produces a change in the mass of layer areas 262a, 262b. The change in mass of sensor 200 results in a change in the operating frequency $f_o$ thereof. Controller 132 monitors the frequency to determine "measured frequencies" $f_m$ during the conditioning phase, during the decontamination phase and during the aeration phase. The measured frequencies $f_m$ are compared to the baseline operating frequency $f_o$ to determine a change in frequency. Controller 132 then determines the concentration of vaporized hydrogen peroxide within chamber 24 at a given point in time by comparing the change in frequency at that given point in time with corresponding data stored in controller 132. Controller 132 is thus able to determine the concentration of hydrogen peroxide ($H_2O_2$) within chamber 24 at a given point in time. In this respect, it is believed that a change in frequency of sensor 200 is directly proportional to a change in concentration of hydrogen peroxide. Thus, the concentration of hydrogen peroxide within chamber 24 can be sensed at a specific point in time, and continuously monitored, based upon a change in frequency of sensor 200.

It should be appreciated that while a preferred embodiment of the present invention has been described with reference to a sterilant comprised of hydrogen peroxide and water, it is contemplated that sterilant comprised of other chemical components may also be used in connection with the present invention. These other chemical components may include deactivating chemicals, including, but not limited to, chemicals selected from the group consisting of: hypochlorites, iodophors, quaternary ammonium chlorides (Quats), acid sanitizers, aldehydes (formaldehyde and glutaraldehyde), alcohols, phenolics, peracetic acid (PAA), and chlorine dioxide.

Specific examples of sterilant chemicals, include, but are not limited to, liquid hydrogen peroxide, peracids such as peracetic acid, bleach, ammonia, ethylene oxide, fluorine containing chemicals, chlorine containing chemicals, bromine containing chemicals, vaporized hydrogen peroxide, vaporized bleach, vaporized peracid, vaporized peracetic acid, ozone, ethylene oxide, chlorine dioxide, halogen containing compounds, other highly oxidative chemicals (i.e., oxidants), and mixtures thereof.

The sterilant chemicals may also be combined with other chemicals, including, but not limited to, water, de-ionized water, distilled water, an alcohol (e.g., a tertiary alcohol), a glycol-containing chemical compound, and mixtures thereof. Glycol-containing chemical compounds include, but are not limited to, polyethylene glycol, diethylene glycol, triethylene glycol, tetraethylene glycol, glycol ethers, polypropylene glycol, propylene glycol, de-ionized water vapor, distilled water vapor, a vaporized alcohol (e.g., a tertiary alcohol), and mixtures thereof. These chemicals may act as carrier fluids or diluents.

The foregoing description is a specific embodiment of the present invention. It should be appreciated that this embodiment is described for purposes of illustration only, and that numerous alterations and modifications may be practiced by those skilled in the art without departing from the spirit and scope of the invention. It is intended that all such modifications and alterations be included insofar as they come within the scope of the invention as claimed or the equivalents thereof.

Having described the invention, the following is claimed:

1. A decontamination system comprising:
   a first source of a first liquid sterilant including a sterilant chemical at a first concentration;
   a second source of a second liquid sterilant including said sterilant chemical at a second concentration;
   first regulating means for regulating a flow rate of the first liquid sterilant;
   second regulating means for regulating a flow rate of the second liquid sterilant;
   a controller including a data storage device for storing a plurality of data values indicative of an electrical property of a first sensor when exposed to a plurality of known concentrations of the sterilant chemical, wherein said controller is programmed to:
   control said first and second regulating means to produce a blended liquid sterilant comprised of the first and second liquid sterilant;
   determine the concentration of the sterilant chemical in the blended liquid sterilant by use of:
   (a) a signal generated by the first sensor when exposed to the blended liquid sterilant, and
   (b) the plurality of data values stored in the data storage device; and
   control the first and second regulating means to produce a blended liquid sterilant having the sterilant chemical at a desired concentration;
   a vaporizer for vaporizing said blended liquid sterilant having the sterilant chemical at the desired concentration to produce a vaporized sterilant; and
   a chamber for receiving said vaporized sterilant.

2. A system according to claim 1, wherein said first sensor is a capacitive sensor, wherein an electrical property of a capacitor is indicative of the concentration of said sterilant chemical in the blended liquid sterilant.

3. A system according to claim 1, wherein said system further comprises a second sensor for sensing concentration of the said sterilant chemical in the vaporized sterilant.

4. A system according to claim 3, wherein said controller is further programmed to control said first and second regulating means in accordance with the concentration of said sterilant chemical in the vaporized sterilant, as sensed by said second sensor.

5. A system according to claim 3, wherein said second sensor includes an element having a layer of a material that is reactive with said sterilant chemical in the vaporized sterilant, such that mechanical movement of the element is converted into an electrical signal indicative of the concentration of said sterilant chemical in the vaporized sterilant.

6. A system according to claim 1, wherein said first concentration is greater than the second concentration.

7. A system according to claim 1, wherein said sterilant chemical is hydrogen peroxide.

8. A system according to claim 1, wherein said second liquid sterilant is comprised of 90% to 100% water, by weight.

9. A system according to claim 1, wherein the concentration of said sterilant chemical in said blended liquid sterilant is in a range defined by said first concentration and said second concentration.

10. A system according to claim 1, wherein said first concentration of said sterilant chemical is in a range of 25% to 75% by weight of said first liquid sterilant.

11. A system according to claim 1, wherein said controller is further programmed to determine the concentration of the sterilant chemical in the blended liquid sterilant by searching the plurality of data values stored in the data storage device according to the signal generated by the first sensor when exposed to the blended liquid sterilant.

* * * * *